United States Patent
Cheng

(10) Patent No.: US 11,105,770 B2
(45) Date of Patent: Aug. 31, 2021

(54) NANOPORE AND DNA SENSOR EMPLOYING NANOPORE

(71) Applicant: INTERNATIONAL BUSINESS MACHINES CORPORATION, Armonk, NY (US)

(72) Inventor: Kangguo Cheng, Schenectady, NY (US)

(73) Assignee: International Business Machines Corporation, Armonk, NY (US)

( * ) Notice: Subject to any disclaimer, the term of this patent is extended or adjusted under 35 U.S.C. 154(b) by 233 days.

(21) Appl. No.: 15/704,677

(22) Filed: Sep. 14, 2017

(65) Prior Publication Data

US 2019/0079048 A1    Mar. 14, 2019

(51) Int. Cl.
| | |
|---|---|
| G01N 27/447 | (2006.01) |
| H01L 21/02 | (2006.01) |
| C12Q 1/6869 | (2018.01) |
| H01L 21/308 | (2006.01) |
| H01L 21/3065 | (2006.01) |

(Continued)

(52) U.S. Cl.
CPC ........ G01N 27/44791 (2013.01); B82Y 15/00 (2013.01); C12Q 1/6869 (2013.01); G01N 27/4473 (2013.01); G01N 33/48721 (2013.01); H01L 21/02164 (2013.01); H01L 21/02236 (2013.01); H01L 21/02255 (2013.01); H01L 21/3065 (2013.01); H01L 21/3081 (2013.01); H01L 21/3085 (2013.01); H01L 21/3086 (2013.01)

(58) Field of Classification Search
CPC ......... H01L 21/02164; H01L 21/02236; H01L 21/02255; H01L 21/3081; H01L 21/3085; H01L 21/3086; H01L 21/3065; G01N 27/44791; G01N 27/4473; C12Q 1/6869
See application file for complete search history.

(56) References Cited

U.S. PATENT DOCUMENTS

| | | |
|---|---|---|
| 4,472,459 A | 9/1984 | Fisher |
| 6,464,892 B2 | 10/2002 | Moon et al. |
| 7,057,274 B2 | 6/2006 | Heschel |

(Continued)

FOREIGN PATENT DOCUMENTS

WO    WO-2016129111 A1 *    8/2016    ............. C23C 16/24

OTHER PUBLICATIONS

Cho, Y.H. et al., "Fabrication of silicon dioxide submicron channels without nanolithography for single biomolecule detection" Nanotechnology (Oct. 2007) pp. 1-6, vol. 18.

(Continued)

*Primary Examiner* — Mayla Gonzalez Ramos
(74) *Attorney, Agent, or Firm* — Tutunjian & Bitetto, P.C.; L. Jeffrey Kelly

(57) ABSTRACT

A method of forming a nanopore that includes forming a pore geometry hard mask on a semiconductor substrate; and oxidizing the semiconductor substrate to form an oxide layer on exposed surfaces of the semiconductor substrate. An apex portion of the oxide layer extends beneath an edge of the pore geometry hard mask. The pore geometry hard mask is removed, and the semiconductor substrate is etched with an etch that is selective to the oxide layer to provide the nanopore. The opening of the nanopore has a diameter defined by the apex portion of the oxide layer.

8 Claims, 4 Drawing Sheets

(51) Int. Cl.
*G01N 33/487* (2006.01)
*B82Y 15/00* (2011.01)

(56) References Cited

U.S. PATENT DOCUMENTS

| | | |
|---|---|---|
| 8,137,569 B2 | 3/2012 | Harnack et al. |
| 8,940,148 B2 | 1/2015 | Afzali-Ardakani et al. |
| 9,034,637 B2 | 5/2015 | Merz et al. |
| 9,057,693 B2 | 6/2015 | Astier et al. |
| 9,679,897 B1 | 6/2017 | Cao et al. |
| 2002/0084249 A1* | 7/2002 | Moon .................. B05B 5/00 216/37 |
| 2007/0117284 A1* | 5/2007 | Imai .................. H01L 21/0214 438/151 |
| 2012/0037591 A1* | 2/2012 | Tringe .............. B01D 67/0062 216/2 |
| 2018/0003673 A1* | 1/2018 | Yanagi .................. C23C 16/24 |

OTHER PUBLICATIONS

Haneveld, J. et al., "Nano-ridge fabrication by local oxidation of silicon edges with silicon nitride as a mask" J. Micromech. Microeng. (May 2006) pp. S24-S28, vol. 16.

* cited by examiner

NANOPORE AND DNA SENSOR EMPLOYING NANOPORE

BACKGROUND

Technical Field

The present disclosure generally relates to nanopore structures, and in some embodiments relates to nanopore structures used for DNA sensors.

Description of the Related Art

Nanopore-based analysis methods often involve passing a polymeric molecule, for example single-stranded DNA ("ssDNA"), through a nanoscopic opening while monitoring a signal such as an electrical signal. As the polymer molecule passes through the nanopore, differences in the chemical and physical properties of the monomeric units that make up the polymer, for example, the nucleotides that compose the ssDNA, are translated into characteristic electrical signals.

SUMMARY

In accordance with one aspect of the present disclosure, a nanopore sensor is provided that includes a substrate having a nanopore present there through, wherein the nanopore has a first width. The nanopore sensor may further include an opening layer providing entry to the nanopore. In some embodiments, the entry of the opening layer has a second width that is less than the first width of the nanopore present extending through the substrate. The entry of the opening layer defined by a reducing thickness to an apex. In some embodiments, the entry to the opening layer is designed to have a size that allows for a polymer material, such as a nucleic acid, e.g., strand of DNA, to pass through the entry of the opening layer only in a sequential, single file order.

In accordance with another aspect of the present disclosure, a method of forming a nanopore is provided that includes forming a pore geometry hard mask on a semiconductor substrate; and oxidizing the semiconductor substrate to form an oxide layer on exposed surfaces of the semiconductor substrate. An apex portion of the oxide layer extends beneath an edge of the pore geometry hard mask. The method may continue with removing the pore geometry hard mask. Thereafter, the semiconductor substrate may be etched with an etch that is selective to the oxide layer to provide the nanopore. In some embodiments, the opening of the nanopore has a diameter defined by the apex portion of the oxide layer. In some embodiments, the entry through the oxide layer defined by the apex portions is designed to have a size that allows for a polymer material, such as a nucleic acid, e.g., strand of DNA, to pass through the entry only in a sequential, single file order.

In another aspect, the present disclosure provides a method of sensing DNA. In one embodiment, the method of sensing DNA includes positioning a nanopore sensor in an electrolytic solution including at least one polymeric molecule. The nanopore sensor includes an opening layer providing entry to a nanopore extending through a substrate, wherein an entry to nanopore through the opening layer is defined by a perimeter having reducing thickness to an apex. A power supply having a first terminal in electrical communication with the electrolytic solution at a first end of the entry to the nanopore, and a second terminal in electrical communication to a second end of the entry to the nanopore. A polymeric molecule having a size suitable for passing through the at least one opening one polymeric molecule at a time is then passed through the entry to the nanopore. The current across the entry to the nanopore is measure as the polymeric material is passed through the entry to the nanopore. Changes in the current measured as the polymer material is passed through the nanopore is correlated to a composition for the polymer material.

These and other features and advantages will become apparent from the following detailed description of illustrative embodiments thereof, which is to be read in connection with the accompanying drawings.

BRIEF DESCRIPTION OF THE DRAWINGS

The following description will provide details of preferred embodiments with reference to the following figures wherein.

DETAILED DESCRIPTION

Figure 1:
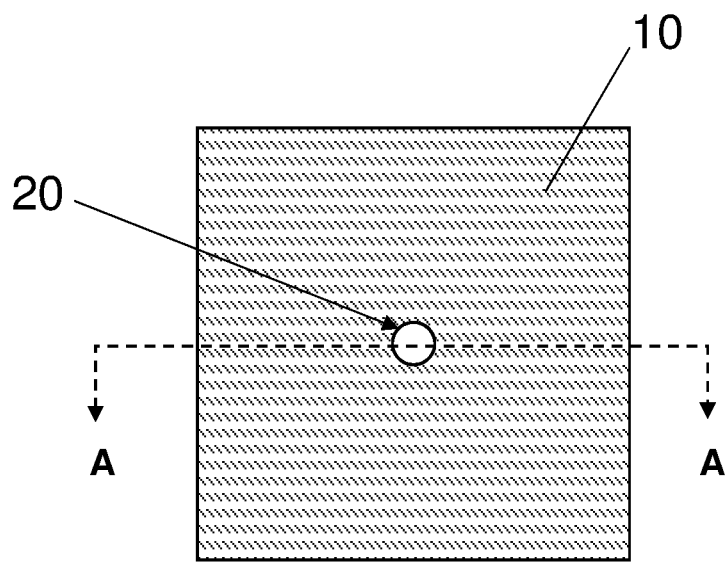
FIG. 1 is a top down view of a nanopore, in accordance with one embodiment of the present disclosure.

Detailed embodiments of the claimed structures and methods are disclosed herein; however, it is to be understood that the disclosed embodiments are merely illustrative of the claimed structures and methods that may be embodied in various forms. In addition, each of the examples given in connection with the various embodiments is intended to be illustrative, and not restrictive. Further, the figures are not necessarily to scale, some features may be exaggerated to show details of particular components. Therefore, specific structural and functional details disclosed herein are not to be interpreted as limiting, but merely as a representative basis for teaching one skilled in the art to variously employ the methods and structures of the present disclosure. For purposes of the description hereinafter, the terms "upper", "lower", "right", "left", "vertical", "horizontal", "top", "bottom", and derivatives thereof shall relate to the embodiments of the disclosure, as it is oriented in the drawing figures. The term "positioned on" means that a first element, such as a first structure, is present on a second element, such as a second structure, wherein intervening elements, such as an interface structure, e.g. interface layer, may be present between the first element and the second element. The term "direct contact" means that a first element, such as a first structure, and a second element, such as a second structure, are connected without any intermediary conducting, insulating or semiconductor layers at the interface of the two elements.

Nanopores have a variety of applications. For example, nanopores have been used to fabricate biosensors for DNA sequencing. Solid state nanopores are attractive as they have the potential to be integrated with semiconductor CMOS. Nanopores can be formed by depositing a thin film (e.g., silicon nitride (SiN)) on a semiconductor substrate followed by patterning to form holes (nanopores) in the film. The semiconductor substrate is then etched from backside to open the nanopore. It has been determined that a number of problems can exist in this approach.

For example, one problem with such an approach is that, the film in which nanopores are formed is processed to be as thin as possible so that tiny bio species, such as single DNA, can be sensed when it passes through the nanopore. It has been determined, that thin films are susceptible to warping, distorting the nanopore dimension and thus compromising the accuracy of the nanopore biosensors.

In some embodiments, the methods and structures described herein provide nanopores that have a thin edge at the perimeter of the entry point to the nanopore, in which the thin edge gradually thickens in a direction away from the center of the entry point of the nanopore to improve the strength of the nanopore film without compromising the requirement of thin nanopore edge. In some embodiments, the nanopore is formed by taking advantage of the bird's beak effect that occurs with the thermal oxidation of silicon. The methods and structures of the present disclosure are now described in greater detail with reference to FIGS. 1-7.

Figure 2:
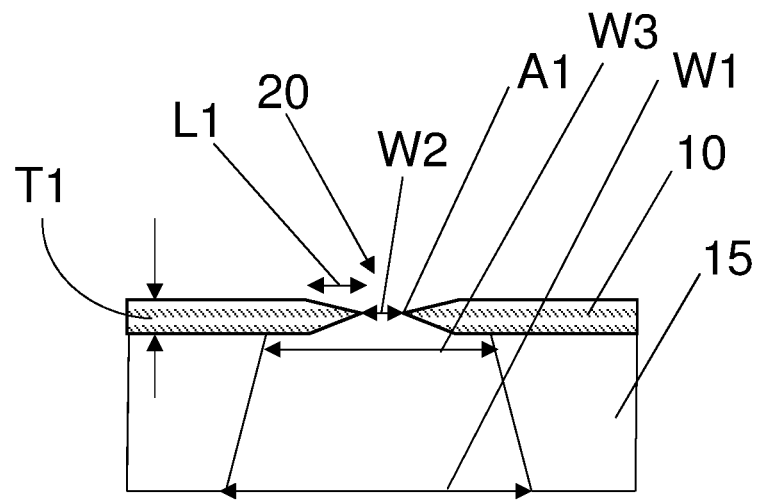
FIG. 2 is a side cross-sectional view of a nanopore depicted in FIG. 1 across section line A-A.

FIGS. 1-2 depict one embodiment of a nanopore sensor 100 that includes a substrate 15 having a nanopore 100 present there through, wherein the nanopore 100 has a first width W1. The nanopore sensor may further include an opening layer 10 providing entry to the nanopore 100. In some embodiments, the entry 20 of the opening layer 10 has a second width W3 that is less than the first width W1 of the nanopore present extending through the substrate. The entry 20 of the opening layer 10 is defined by a reducing thickness to an apex.

In some embodiments, the nanopore sensor includes a substrate 15 having a nanopore 100 present there through. The nanopore 100 that is present through the substrate 15 has a first width W1 that is of a nano-dimension. The term nano-dimension means that the first width W1 has a value of 1 micron or less. An opening layer 10 is present atop the substrate 15 through which the nanopore 100 extends. The opening layer 10 provides the entry 20 to the nanopore 100. The entry 20 through the opening layer 10 has a second width W2 that is less than the first width W1 of the nanopore 20 that is present extending through the substrate 15. In some embodiments, the entry 20 through the opening layer 10 also has a width W2 of a nano-dimension. In some embodiments, the entry 20 to the nanopore 100 is defined by a diameter portion of the opening layer 10 that has a reducing thickness to an apex A1. The thinnest portion of the opening 10 is present at the edges of the entry 20 to the nanopore 100.

In some embodiments, the substrate 15 may be composed of a type IV semiconductor. The semiconductor substrate 15 may be a bulk-semiconductor substrate. In one example, the bulk-semiconductor substrate may be a silicon-containing material or other type IV semiconductor material. Illustrative examples of Si-containing materials suitable for the bulk-semiconductor substrate include, but are not limited to, Si, SiGe, SiGeC, SiC, polysilicon, i.e., polySi, epitaxial silicon, i.e., epi-Si, amorphous Si, i.e., α:Si, and multi-layers thereof. Alternative semiconductor materials can also be employed, such as, but not limited to, germanium, gallium arsenide, gallium nitride, silicon germanium, cadmium telluride and zinc sellenide. Although not depicted in FIG. 1, the semiconductor substrate 15 may also be a semiconductor on insulator (SOI) substrate. The semiconductor on insulator (SOI) substrate may include at least a first semiconductor layer (also referred to as a semiconductor on insulator (SOI) layer) overlying a dielectric layer, in which a base semiconductor layer may be present underlying the dielectric layer. The semiconductor material that provides the semiconductor on insulator layer may be any semiconducting material, such as the above examples for the semiconductor material of a bulk semiconductor substrate. The base semiconductor layer may have the same or a different composition than the semiconductor on insulator layer. The dielectric layer, i.e., buried dielectric layer, can be composed of any dielectric material, such as an oxide, e.g., silicon oxide. The dielectric layer, i.e., buried dielectric layer, that may be present underlying the semiconductor on insulator layer and atop the base semiconductor layer may be formed by implanting a high-energy dopant into a bulk semiconductor substrate and then annealing the structure to form a buried insulating layer. In another embodiment, the dielectric layer may be deposited or grown prior to the formation of the semiconductor on insulator layer. In yet another embodiment, the semiconductor on insulator substrate may be formed using wafer-bonding techniques, where a bonded wafer pair is formed utilizing glue, adhesive polymer, or direct bonding.

As noted above, the nanopore 100 extends through the semiconductor substrate 15. This means that the nanopore 100 has a first end at a first face, e.g., upper face, of the semiconductor substrate 15, and a second end at a second face, e.g., back face, of the semiconductor substrate 15, in which a passageway through the semiconductor substrate 15 extends continuously from the first end to the second end. The opening layer 10 is present on, e.g., in direct contact with, the first face of the semiconductor substrate 15, at which the first end of the nanopore 100 is present. The nanopore 100 has a width W3 at the first face of the semiconductor substrate 15 that is greater than the width W2 of the opening 20 provided by the opening layer 10. The nanopore 100 typically has a width at a nanoscale dimension. In some embodiments, the width W3 of the nanopore 100 at the first face of the semiconductor substrate 15 may range from 10 nm to 100,000 nm. In some other embodiments, the width W3 of the nanopore 100 at the first face of the semiconductor substrate 15 may range from 10 nm to 10,000 nm.

The nanopore 100 has a width W1 at the second face of the semiconductor substrate 15 that is also greater than the width W2 of the opening 20 provided by the opening layer 10. The width W1 of the nanopore 100 of the second face of the semiconductor substrate 15 is also of a nanoscale dimension. For example, the width W1 of the nanopore 100 at the second face of the semiconductor substrate 15 may range from 20 nm to 100,000 nm. In some other embodiments, the width W1 of the nanopore 100 at the second face of the semiconductor substrate 15 may range from 20 nm to 10,000 nm.

In some embodiments, the width W1 of the nanopore 100 at the second face of the semiconductor substrate 15 is greater than the width W3 of the nanopore 100 at the first face of the semiconductor substrate 15 to provide that the width of the nanopore 100 increases in a direction through the passageway of the nanopore from the opening 20 provided by the opening layer 10.

Still referring to FIGS. 1 and 2, the opening layer 10 that is present atop the semiconductor substrate 15 may be composed of a dielectric material. The dielectric material of the opening layer 10 may be any dielectric that can be formed using a thermal process that produces bird beak type edges. Bird beak edges are characterized by a thickness that reduces from the thickness of the material layer that is present on a semiconductor substrate 15 to an apex A1. In some embodiments, the opening layer 10 may be composed of an oxide. The oxide of the opening layer 10 is formed directly on the semiconductor substrate 15, and therefore can include an element of the semiconductor substrate 15. For example, when the semiconductor substrate 15 includes silicon (Si), such as a monocrystalline silicon (Si) substrate, the oxide of the opening layer 10 may be silicon oxide ($SiO_2$). Other oxides may be equally applicable for the composition of the opening layer 10. For example, the opening layer 10 may also be composed of silicon oxynitride ($SiO_xN_y$).

The composition for the opening layer 10 is selected to allow for the opening layer 10 to be formed using an oxidation process that forms "birds beaks" at an interface of the semiconductor substrate 15 and an etch mask, such as a hard mask composed of silicon nitride. As will be described in further detail below, during oxidation of the semiconductor substrate to form the opening layer 10, the availability of an oxidant diffusion path in the semiconductor substrate 15 under a nitride mask (the pad oxide) that is utilized during the oxidation process, provides for lateral oxidation of the semiconductor substrate that forms the apex portions A1 of the opening layer 10. More specifically, the opening layer 10 can by a dielectric layer, such as an oxide, e.g., silicon oxide, having a first portion with a first thickness T1 directly on the semiconductor substrate 15, and a second portion having a reducing thickness to the entry 20 of the nanopore 100 at which the apex A1 is present.

The first thickness T1 of the opening layer 10 may range from 5 nm to 75 nm. In another embodiment, the first thickness T1 of the opening layer 10 may range from 5 nm to 50 nm. In yet another embodiment, the first thickness T1 of the opening layer 10 may range from 15 nm to 30 nm.

The apex portions have a length L1 that begins at the end edges of the portions of the opening layer 10 having the first thickness T1, i.e., the edges at which the thickness opening layer 10 begins to be reduced, and ends at the apex A1 of the opening layer 10, which ends in a point. The length L1 of the apex portions for the opening layer 10 may range from 5 nm to 200 nm. In some other embodiments, the length L1 of the apex portions for the opening layer 10 may range from 10 nm to 100 nm. The reduction in the thickness of the apex portions to their point, i.e., apex, provides that the side-cross section of the apex portion of the opening layer 10 has a substantially triangular shape.

The dimensions for the entry 20 to the nanopore 100 is defined by the apex A1 of the opening layer 10. As illustrated above, the apex A1 defines the substantially circular geometry for the entry 20 to the nanopore 100. The width W2 of the entry 20 is defined from one apex A1 at a first side of the entry 20 to a second apex at a second side of the entry 20. The width of the entry 20 is selected to have a dimension that will only allow for one protein to be measured by a sensor using the nanopore structure to pass through the entry 20 of the nanopore 100 at a time. In some embodiments, the width W2 of the entry 20 may range from 1 nm to 10 nm. In some examples, the width W2 of the entry 20 that is defined by the apex to apex dimension across the nanopore 100 may be equal to 1 nm, 1.5 nm, 2 nm, 2.5 nm, 3 nm, 3.5 nm. 4 nm, 4.5 nm, 5 nm, 5.5, nm, 6 nm, 6.5 nm, 7 nm, 7.5 nm, 8 nm, 8.5 nm, 9 nm, 9.5 nm and 10 nm, as well as any range for the width W2 dimension including an upper level and a lower level that is selected from the above provided example dimensions. For example, in some other embodiments, the width W2 of the entry 20 range from 1.5 nm to 5 nm.

The nanopore structure that is depicted in FIGS. 1 and 2 is now described in more detail with reference to FIGS. 3-6, which depict some examples of images corresponding to method steps for forming a nanopore structure that in some embodiments can be used for in nanopore detector. For example, a nanopore detector that employs the nanopore structure depicted in FIGS. 1-6 can be suitable for sensing polymeric compositions, e.g., DNA compositions.

In some embodiments, the method that is described with reference to FIGS. 1-6 can provide a nanopore 100 including an opening layer 10 at a semiconductor substrate 15 through which the nanopore 100 extends. The portion of the opening layer 10 that provides the entry 20 to the nanopore 100 has apex A1 portions with a reducing thickness to that provides an entry 20 with a substantially circular perimeter, and a width dimension that is selected to allow for one polymeric entity at a time to pass through the entry 20 to the nanopore 100.

Figure 3:
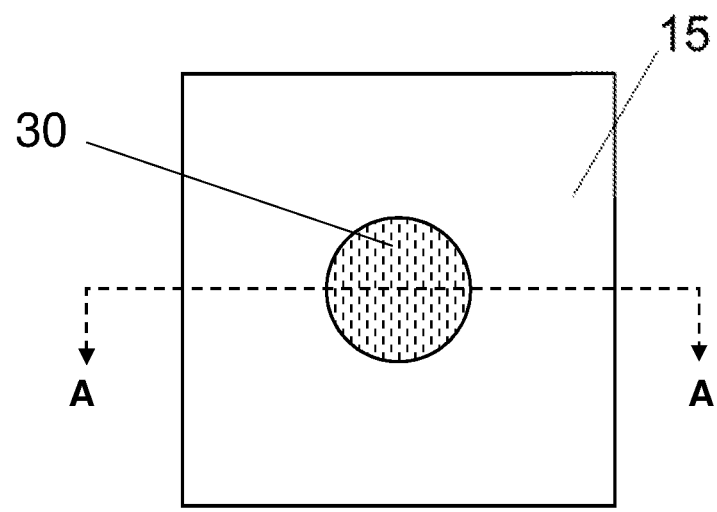
FIG. 3 is a top down view of forming a pore geometry hard mask on a semiconductor substrate, in accordance with one embodiment of a method of forming a nanopore.
Figure 4:
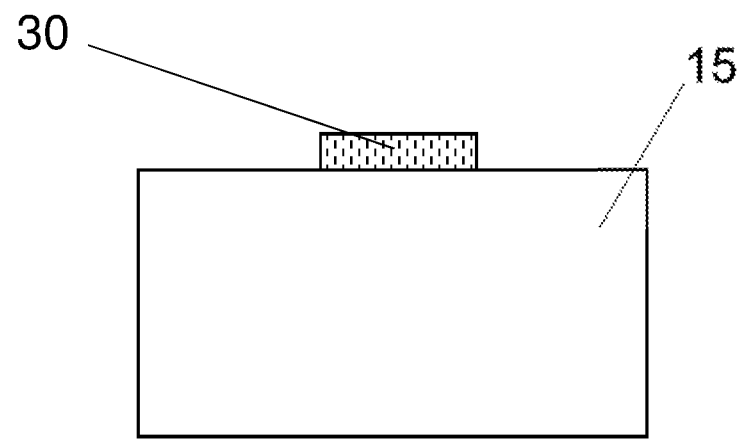
FIG. 4 is a side cross-sectional view of the hard mask atop the semiconductor substrate along section line A-A.

Referring to FIGS. 3 and 4, the method may being with forming a mask 30 on the portion of the semiconductor substrate 15 in which the nanopore 100 is to be formed. The mask 30 may be a hardmask. The hardmask can be formed using deposition, photolithography and etching. In some embodiments, the hardmask is a mask 30 that is composed of a nitride containing dielectric material. The nitride containing dielectric material for providing the mask 30 can be deposited using a chemical vapor deposition (CVD) process. The nitride containing dielectric material is blanket deposited atop an entirety of the semiconductor substrate 15.

Chemical vapor deposition (CVD) is a deposition process in which a deposited species is formed as a result of chemical reaction between gaseous reactants at greater than room temperature (25° C. to 900° C.), wherein solid product of the reaction is deposited on the surface on which a film, coating, or layer of the solid product is to be formed. Variations of CVD processes include, but not limited to, Atmospheric Pressure CVD (APCVD), Low Pressure CVD (LPCVD) and Plasma Enhanced CVD (PECVD), Metal-Organic CVD (MOCVD) and combinations thereof may also be employed. In addition to chemical vapor deposition (CVD), the nitride containing dielectric material that is blanket deposited for forming the mask 30 may also be formed using a spin-on process.

In one example, the nitride containing dielectric layer is composed of silicon nitride. In another example, the nitride containing dielectric layer is composed of silicon oxynitride. The thickness of the nitride containing dielectric layer may range from 1 nm to 10 nm. In another embodiment, the thickness of the nitride containing dielectric layer may range from 2 nm to 10 nm. In one example, the nitride containing dielectric layer is compose of silicon nitride having a 5 nm thickness.

Following deposition of the layer of hardmask material, i.e., nitride containing dielectric layer, a patterned photoresist (not shown) is formed atop the layer of hardmask material, and the layer of hardmask material is etched to provide the mask 30, e.g., hardmask. A patterned photoresist can be produced by applying a photoresist layer the surface of the layer of hardmask material, i.e., nitride containing dielectric layer, exposing the photoresist layer to a pattern of radiation, and then developing the pattern into the photoresist layer utilizing resist developer.

Still referring to FIGS. 3 and 4, the method may continue with removing the exposed portions of the hardmask material, i.e., nitride containing dielectric layer, while the portions of the nitride containing dielectric layer that are underlying photoresist mask remain to provide the mask 30, e.g., hardmask. In some embodiments, the exposed portions of the hardmask material are removed by an etch process. For example, the etch process may be an anisotropic etch, i.e., directional etch, such as reactive ion etching (RIE). In some embodiments, the etch process can use an etch chemistry for removing the exposed portions of the hardmask material that has a high selectivity to the patterned photoresist and the semiconductor substrate 15. As used herein, the term "selective" in reference to a material removal process denotes that the rate of material removal for a first material is greater than the rate of removal for at least another material of the structure to which the material removal process is being applied. For example, in one embodiment, a selective etch may include an etch chemistry that removes a first material selectively to a second material by a ratio of 100:1 or greater.

The mask 30 that is depicted in FIGS. 3 and 4 may have a pore geometry. For example, the top down view geometry of the mask may be substantially circular. The diameter for the mask 30 may be from 1 nm to 100 nm. In one embodiment, the mask 30 may have a diameter ranging from 2 nm to 50 nm.

Figure 5:
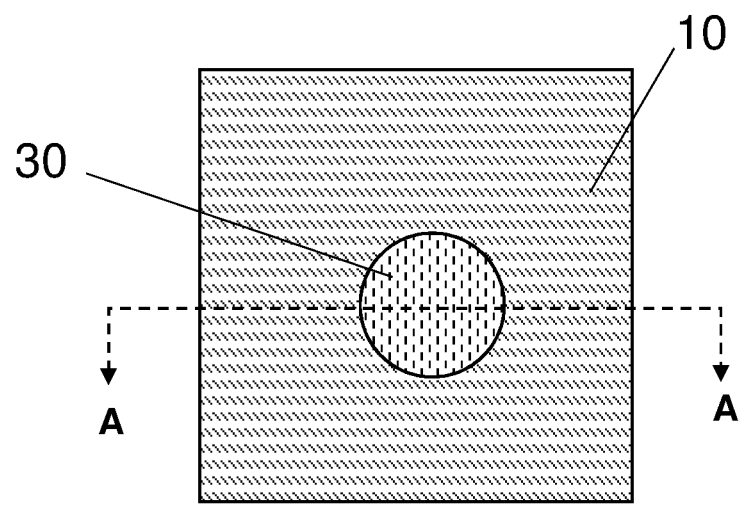
FIG. 5 is a top down view depicting one embodiment of oxidizing the semiconductor substrate that is depicted in FIG. 3 to form an oxide layer on exposed surfaces of the semiconductor substrate, wherein an apex portion of the oxide layer extends beneath an edge of the pore geometry hard mask.
Figure 6:
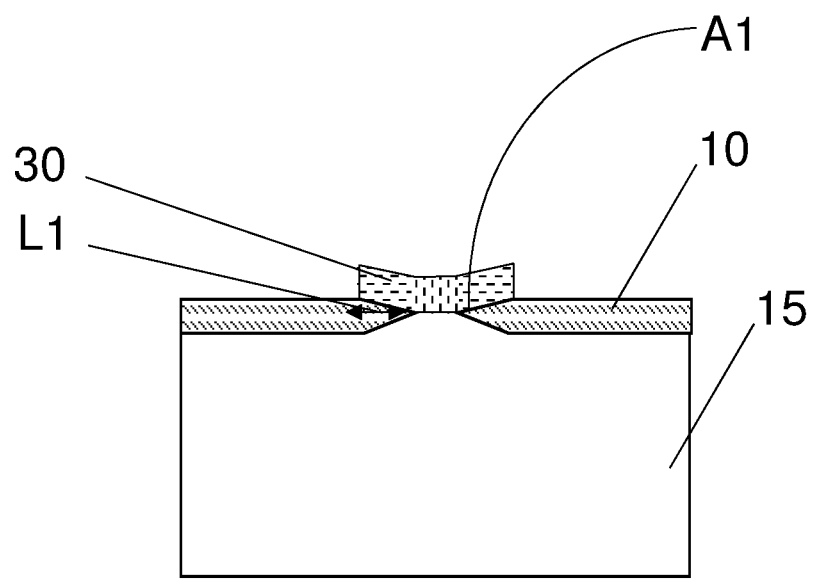
FIG. 6 is a side cross-sectional view of the structure depicted in FIG. 5 along section line A-A.

FIGS. 5 and 6 depict one embodiment of oxidizing the semiconductor substrate 15 that is depicted in FIGS. 3 and 4 to form an opening layer 10, also referred to as oxide layer 10, on exposed surfaces of the semiconductor substrate 15. The apex portion A1 of the opening layer 10/oxide layer 10 extends beneath an edge of the pore geometry hard mask 30.

In some embodiments, in which the semiconductor substrate 15 is composed of silicon (Si), the oxidizing of the semiconductor substrate 15 is provided by local oxidation of silicon (LOCOS). Local oxidation of silicon (LOCOS) is a thermal oxidation, where oxygen diffuses to an interface with substantially pure silicon i.e., the upper surface of the semiconductor substrate 15, at which the silicon reacts with the oxygen to form a new dioxide, e.g., silicon dioxide. The formation of silicon dioxide can result in yielding strains due to the larger volume of the dioxide.

The oxygen source for thermal oxidation may be any oxygen source such as gaseous oxygen ($O_2$) that is present in an oxygen containing atmosphere, such as an annealing atmosphere or ambient atmosphere, or may be introduced to the portions of the semiconductor substrate 15 to be oxidized by a liquid, such as water ($H_2O$). In some embodiments, the oxygen containing liquid can be vaporized and misted to the portions of the surface of the semiconductor substrate 15 to be oxidized. In other embodiments, the oxygen containing liquid, e.g., water ($H_2O$), can be brushed or sprayed on the surface of the semiconductor substrate 15. Besides thermal oxidation, other oxidation techniques such as plasma oxidation, ozone oxidation (oxidation in $O_3$ environment) can be used.

The thickness of the oxide layer 10 may range from 1 nm to 100 nm. In another embodiment, the thickness of the oxide layer can range 5 nm to 50 nm. Oxidation can take place at room temperature, e.g., 20° C. to 25° C., resulting in a thin oxide growth of approximately 1 nm in height. The oxidation cannot proceed further at room temperature, because the oxygen molecules (O), which are the main contributors of oxygen in the oxidation process, do not have enough energy to diffuse through the 1 nm thick oxide. In some embodiments, to provide the appropriate thickness for the oxide layer 10, the temperature of the oxidation process can range from 500° C. to 1300° C. In other embodiments, the temperature for the oxidation process can range from 1000° C. to 1100° C.

Referring to FIGS. 5 and 6, as the oxygen diffuses through the oxide already formed, the diffusing oxygen can oxidize the silicon of the semiconductor substrate 15 that is underlying the mask 30, the hardmask 30 that is composed of silicon nitride. This is a form of lateral oxidation, i.e., oxidation in a directly parallel to the upper surface of the semiconductor substrate 15. Since a given volume of silicon expands by almost a factor of 2 upon oxidation, e.g., oxidizing 1 $cm^3$ of silicon produces almost 2 $cm^3$ of $SiO_2$, the nitride mask is pressed upwards at the edges as illustrated.

One aspect of LOCOS which can be noted from FIG. 6 is that, as the oxide grows, the mask 30, e.g., nitride hardmask, bends to generate a "bird's beak" effect as the oxide is pinched under the nitride mask at the edges. In the beginning of the field oxidation, the oxide growth is limited by the surface reaction rate and the oxidation rate under the mask 30, i.e., silicon nitride hardmask, will be approximately equal to the oxidation rate in the field region. As the oxide thickness increases, the oxidation becomes diffusion limited and the amount of oxidants reaching the silicon surface under the nitride mask is limited by the lifting of the nitride mask.

The length of the birds beak can on the silicon crystal orientation, mainly due to the difference in the amount of silicon available for bonding at the (111) surface compared to the (100) surface. Further, the length of the bird's beak can be increased by increasing the thermal oxidation temperature, i.e., increasing the diffusion of oxygen; and the length of the birds beak can be decreased by decreasing the thermal oxidation temperature, i.e., decreasing the diffusion of oxygen.

In some embodiments, the length L1 of the birds beak (also referred to as apex portions) for the oxide layer 10/opening layer 10 may range from 5 nm to 200 nm. In some other embodiments, the length L1 of the apex portions for the oxide layer 10/opening layer 10 may range from 10 nm to 100 nm.

In some embodiments, the opening (referred to as entry 20) to the subsequently formed nanopore 100 has a diameter defined by the apex portion of the oxide layer 10/opening 10. As illustrated in FIG. 6, the lateral oxygen diffusion in the formation of the bird beak portion of the oxide layer 10 that extends under the mask 30 ceases to provide that the apex of the bird beak on one side of the mask 30 is separated, i.e., does not touch, the apex of the bird beak on the opposing side of the mask 30. As will be described below, in following process steps, the silicon of the semiconductor substrate 15 that has not been oxidized, and is present between the apex portions of the oxide layer 10, is removed selectively to the oxide layer 10 to provide the entry 20 to the nanopore. Therefore, the portion of the semiconductor substrate 15, i.e., silicon material that has not oxidized, present between the opposing apex of the bird beak portions of the oxide layer 10/opening layer 10 define the dimensions and geometry of the entry 20 to the nanopore.

The bird beak portion of the oxide layer 10/opening layer 10 has an apex that provides the geometry of the entry 20 to the nanopore 100. The oxide layer 10/opening layer 10 has a thinnest portion at the edges of the entry 20 to the nanopore, in which the oxide layer 10/opening 10 gradually thickens away from nanopore. The thin oxide apex, i.e., bird beak portion of the oxide layer 10/opening layer 10, enables single polymeric species/DNA sensing.

The method may continue with removing the pore geometry hard mask 30. The pore geometry hard mask 30 may be removed using a selective etch process that removes the mask 30 selectively to the oxide layer 10/opening layer 10. The etch process for removing the mask 30 may be an anisotropic etch, such as reactive ion etch (RIE), and/or wet chemical etch.

Thereafter, the semiconductor substrate 15 may be etched with an etch that is selective to the opening layer 10/oxide layer 10 to form the nanopore 100 through the semiconductor substrate 15, as depicted in FIGS. 1 and 2. The etch process for forming the nanopore 100 may be an isotropic etch. The isotropic and selective nature of the etch process for forming the nanopore 100 provides that the width W1, W3 of the nanopore 100 through the semiconductor substrate 15 is greater than the width W2 of the entry 20 to the nanopore 100 that is provided by the pore shaped geometry defined by the apex of the opening layer 10/oxide layer 10. The etch process for forming the nanopore 100 may be a gas plasma etch and/or wet chemical etch.

Figure 7:
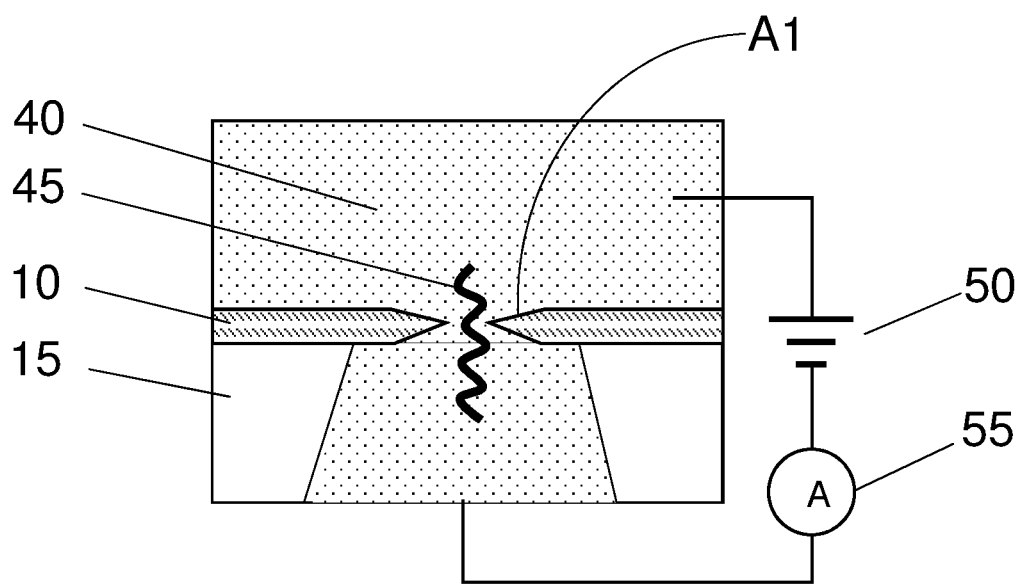
FIG. 7 is a side cross sectional view of a nanopore detector as depicted in FIG. 1 used to detect polymeric materials from an electrolytic solution, in accordance with one embodiment of the present disclosure.

The nanopore 100 that is described above with reference to FIGS. 1-6 is suitable for providing a sensor 500 for detecting polymeric composition and DNA sequences. FIG. 7 illustrates one embodiment of a nanopore detector 500 including a nanopore 100 as described above with reference to FIGS. 1-6 used to detect polymeric materials 45 from an electrolytic solution 40. An electrolyte solution 40 is a solution that generally contains ions, atoms or molecules that have lost or gained electrons, and is electrically conductive. For this reason they are often called ionic solutions, however there are some cases where the electrolytes are not ions. In some embodiments, the electrolytic solution 40 is an aqueous solution. In some embodiments, the electrolytic solution 40 contains salts. A salt is an ionic compound that can be formed by the neutralization reaction of an acid and a base. Salts can be composed of related numbers of cations (positively charged ions) and anions (negative ions) so that the product is electrically neutral (without a net charge). One example of a salt is sodium chloride (NaCl).

The polymeric material 45 that can be sense by the nanopore detector 500 may be nucleic acids. Nucleic acids are biopolymers, or biomolecules, for all known forms of life. They are composed of monomers, which are nucleotides made of three components: a 5-carbon sugar, a phosphate group, and a nitrogenous base. "Nucleic acid" shall mean any nucleic acid molecule, including, without limitation, DNA, RNA and hybrids thereof. The nucleic acid bases that form nucleic acid molecules can be the bases adenine (A), cytosine (C), guanines (G), thymines (T) and uracil (U), as well as derivatives thereof. "Type" of nucleotide refers to adenine (A), cytosine (C), guanines (G), thymines (T) and uracil (U). The specific order of how these nucleotides are arranged is the code for biological phenomena. In some embodiments, the nanopore detector 500 can determine the sequence of the nucleotides from electrical readings measured as the polymeric material 45, e.g., nucleic acid, passes through the entry 20 to the nanopore 100 of the nanopore detector 500. The dimensions of the entry 20 to the nanopore 100 are provide so that each segment of polymeric material 45 passes through the entry 20 one segment at a time.

In some embodiments, the nanopore detector 500 also includes a power supply 50 having a first terminal in electrical communication with the electrolytic solution 40 at a first end of the entry 20 to the nanopore, and a second terminal in electrical communication to a second end of the entry 20 to the nanopore 100. The nanopore detector 500 may also include a current meter 55 for measuring current as the polymeric material 45 is passed one strand of material, e.g., strand of nucleic acid material, through the entry 20 at a time.

In one embodiment, the nanopore detector 500 may be employed in a method of sensing DNA that includes positioning a nanopore sensor 500 in a electrolytic solution 40 including at least one polymeric molecule 45, e.g., at least one strand of nucleic acid, e.g., DNA. The nanopore sensor 500 includes an opening layer 10 providing entry 20 to a nanopore 100 extending through a substrate 15. In some embodiments, the entry 20 to nanopore 100 through the opening layer is defined by a perimeter having reducing thickness to an apex.

A power supply 50 is connected to the electrolytic solution 40, the power supply 50 having a first terminal in electrical communication with the electrolytic solution 40 at a first end of the entry 20 to the nanopore 100, and a second terminal in electrical communication to a second end of the entry 20 to the nanopore 100. Ion current through the nanopore 100 by the current meter 55. Without the polymeric molecule 45, e.g., at least one strand of nucleic acid, e.g., DNA, in the nanopore 100, the ion current is high (reference current). Measuring the current through the nanopore 100 without a polymeric molecule 45, e.g., at least one strand of nucleic acid, e.g., DNA, in the nanopore 100 may be referred to as establishing a reference current.

In a following step, a polymeric molecule 45, e.g., at least one strand of nucleic acid, e.g., DNA, having a size suitable for passing through the at least one opening, i.e., entry 20, of the opening layer 10/oxide layer 10 one polymeric molecule at a time is then passed through the entry 20 to the nanopore 100. The current across the entry 20 to the nanopore 100 is measure as the polymeric material 45 is passed through the entry 20 to the nanopore 100. Changes in the current measured as the polymer material 45 is passed through the nanopore 100 is correlated to a composition for the polymer material 45. In some embodiments, when DNA passes through nanopore 100, it reduces the ion current (relative to the reference current) that is measured by the current meter 55 attached to the power source 50. The amount of ion current reduction depends on the type of DNA. For example, each nucleotide of type adenine (A), cytosine (C), guanines (G), thymines (T) and uracil (U) can have a different value of ion current reduction. As a single polymeric material 45, e.g., single strand of nucleic acid (single strand of DNA), is passed through the entry 20 to the nanopore 100 on strand or element at a time, the different measurements in changes in ion current reduction can be corrected to the different nucleotide types, hence providing one example of sequencing.

It is to be appreciated that the use of any of the following "/", "and/or", and "at least one of", for example, in the cases of "A/B", "A and/or B" and "at least one of A and B", is intended to encompass the selection of the first listed option (A) only, or the selection of the second listed option (B) only, or the selection of both options (A and B). As a further example, in the cases of "A, B, and/or C" and "at least one of A, B, and C", such phrasing is intended to encompass the selection of the first listed option (A) only, or the selection of the second listed option (B) only, or the selection of the third listed option (C) only, or the selection of the first and the second listed options (A and B) only, or the selection of the first and third listed options (A and C) only, or the selection of the second and third listed options (B and C) only, or the selection of all three options (A and B and C). This can be extended, as readily apparent by one of ordinary skill in this and related arts, for as many items listed.

The terminology used herein is for the purpose of describing particular embodiments only and is not intended to be limiting of example embodiments. As used herein, the singular forms "a," "an" and "the" are intended to include the plural forms as well, unless the context clearly indicates otherwise. It will be further understood that the terms "comprises," "comprising," "includes" and/or "including," when used herein, specify the presence of stated features, integers, steps, operations, elements and/or components, but do not preclude the presence or addition of one or more other features, integers, steps, operations, elements, components and/or groups thereof.

Spatially relative terms, such as "beneath," "below," "lower," "above," "upper," and the like, can be used herein for ease of description to describe one element's or feature's relationship to another element(s) or feature(s) as illustrated in the FIGS. It will be understood that the spatially relative terms are intended to encompass different orientations of the device in use or operation in addition to the orientation depicted in the FIGS. For example, if the device in the FIGS. is turned over, elements described as "below" or "beneath" other elements or features would then be oriented "above" the other elements or features. Thus, the term "below" can encompass both an orientation of above and below. The device can be otherwise oriented (rotated 90 degrees or at other orientations), and the spatially relative descriptors used herein can be interpreted accordingly. In addition, it will also be understood that when a layer is referred to as being "between" two layers, it can be the only layer between the two layers, or one or more intervening layers can also be present.

It will be understood that, although the terms first, second, etc. can be used herein to describe various elements, these elements should not be limited by these terms. These terms are only used to distinguish one element from another element. Thus, a first element discussed below could be termed a second element without departing from the scope of the present concept.

Having described preferred embodiments of a system and method of a nanopore and DNA sensor employing the nanopore (which are intended to be illustrative and not limiting), it is noted that modifications and variations can be made by persons skilled in the art in light of the above teachings. It is therefore to be understood that changes may be made in the particular embodiments disclosed which are within the scope of the invention as outlined by the appended claims. Having thus described aspects of the invention, with the details and particularity required by the patent laws, what is claimed and desired protected by Letters Patent is set forth in the appended claims.

The invention claimed is:

1. A method of forming a nanopore comprising:
    forming a pore geometry hard mask on a semiconductor substrate;
    oxidizing the semiconductor substrate to form an oxide layer on exposed surfaces of the semiconductor substrate, said oxidizing causing expansion of semiconductor material of said semiconductor substrate at an interface of the pore geometry hardmask and the semiconductor substrate to cause lift up of edges of the pore geometry hardmask to accelerate oxidation of the oxide layer to provide an apex portion of the oxide layer of reducing thickness to a peak, and an apex portion of the oxide layer extends beneath an edge of the pore geometry hard mask;
    removing the pore geometry hard mask; and
    etching the semiconductor substrate with an etch that is selective to the oxide layer to provide the nanopore, the opening of the nanopore having a diameter defined by an edge of the apex portion of the oxide layer having said peak, and a through opening that is present underlying the opening of the nanopore that has said diameter defined by the edge of the apex portion of the oxide layer, in which the through substrate opening has a greater diameter than the opening of the nanopore defined by the edge of the apex portion of the oxide layer and the through substrate opening extends through an entire thickness of the semiconductor substrate to provide a continuous opening extending from an entry to the opening of the nanopore through the nanopore and the substrate opening through the entire thickness of the semiconductor substrate.

2. The method of claim 1, wherein forming the pore geometry hard mask comprises:
    forming a nitride layer of the semiconductor substrate;
    forming an etch mask having said pore geometry on the nitride layer;
    etching the nitride layer with an etch that is selective to the semiconductor substrate; and
    removing the etch mask.

3. The method of claim 2, wherein the pore geometry hard mask is substantially circular and has a diameter ranging from 1 nm to 10 nm.

4. The method of claim 1, wherein oxidizing the semiconductor substrate comprises heating the semiconductor substrate at a temperature ranging from 500° C. to 1300° C. in an oxygen containing atmosphere.

5. The method of claim 1, wherein oxidizing the semiconductor substrate comprises applying an oxygen containing vapor, plasma or gas to the semiconductor substrate.

6. The method of claim 1, wherein the apex comprises an edge defining the diameter of the opening of the nanopore, the apex having an increasing thickness from the edge to a remainder of the oxide layer.

7. The method of claim 1, wherein the oxide layer comprises silicon oxide.

8. The method of claim 1, wherein the diameter defined by the apex portion of the oxide layer that provides the opening to the nanopore ranges from 1.5 nm to 5.0 nm.

* * * * *